(12) United States Patent
Tsai et al.

(10) Patent No.: US 7,500,378 B2
(45) Date of Patent: Mar. 10, 2009

(54) MICRO-IMPACT TESTING APPARATUS

(75) Inventors: Kuo Tsing Tsai, Singapore (SG); Ee Hua Wong, Singapore (SG); Ranjan s/o Rajoo, Singapore (SG)

(73) Assignees: Agency for Science Technology and Research, Centros (SG); Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 11/793,634

(22) PCT Filed: Apr. 27, 2006

(86) PCT No.: PCT/SG2006/000107

§ 371 (c)(1),
(2), (4) Date: Jun. 20, 2007

(87) PCT Pub. No.: WO2006/118545

PCT Pub. Date: Nov. 9, 2006

(65) Prior Publication Data

US 2008/0141783 A1    Jun. 19, 2008

(51) Int. Cl.
*G01M 7/00* (2006.01)
(52) U.S. Cl. .................... 73/12.09; 73/12.01
(58) Field of Classification Search ...... 73/12.01–12.14
See application file for complete search history.

(56) References Cited

U.S. PATENT DOCUMENTS 3,939,691 A * 2/1976 Stanev et al. ............ 73/12.01

(Continued)

FOREIGN PATENT DOCUMENTS

EP    A-1 306 350    5/2003

OTHER PUBLICATIONS

Database Compendex [Online] Engineering Information, Inc., New York, NY, US; Reinikainen TO et al. "Deformation characteristics and microstructural evolution of SnAgCu solder" XP002395188 Database accession no. E2006289990 130.

(Continued)

*Primary Examiner*—Max Noori
(74) *Attorney, Agent, or Firm*—Day Pitney LLP (57) ABSTRACT

A micro-impact testing apparatus for measuring the impact characteristics of a microelectronics specimen exposed to an impact thereon. The apparatus comprises of a specimen holder for receiving a specimen to be tested, and an impact device. The impact device comprises of an impact head, a support member, at least one connecting element and a first flexural spring. The support member is connected to the connecting element in that the first flexural spring is firmly attached with its one end to the support member and with its other end to the connecting element. A second flexural spring, being at least substantially identical to said first flexural spring, is firmly attached with its one end to the connecting element and with its other end to the impact head so that the ends of the first and second flexural springs define, in an unloaded state of the flexural springs, a rectangle. The impact head is moveable transversally with respect to the first and second flexural springs along a linear line between a spring-loaded position and an impact position thereof. The specimen holder is aligned with the impact device such that the specimen is arranged in said impact position of the impact head so that the impact head is capable of impacting on the specimen after traveling from its loaded position towards its impact position along said linear line upon release thereof from said loaded position.

19 Claims, 10 Drawing Sheets

U.S. PATENT DOCUMENTS

| | | | | |
|---|---|---|---|---|
| 4,330,944 | A | * | 5/1982 | Maisenbacher et al. ... 33/199 R |
| 6,526,813 | B1 | * | 3/2003 | Casler ........................... 73/82 |
| 7,041,257 | B2 | * | 5/2006 | Gilbert et al. ............... 422/100 |
| 7,219,531 | B2 | * | 5/2007 | Hammons et al. .......... 73/12.13 |

OTHER PUBLICATIONS

Jonnaiagadda Krishna et al. "Mechanical bend fatigue reliability of lead free and halogen-free PBGA Assemblies" IEEE Trans. Compn. Packag. Technol.; IEEE Transactions On Components and Packaging Technologies Sep. 2005, vol. 28, No. 3, Sep. 2005 (Sep. 2005), pp. 430-434, XP002395183.

Database Compendex [Online] Engineering Information, Inc., New York, NY, US: Kim Choong-Un et al.; "Bending fatigue test as a reliability evaluation method for solder joints" XP002395189 Database accession no. E2005179064617.

Database Compendex [Online] Engineering Information, Inc., New York, NY, US; Lee Shi-Wei Ricky et al.; "Experimental evaluation on solder joint reliability of P8GA assembly under mechanical drop test" XP002395190 Database accession no. E2004037818011.

Database Compendex [Online] Engineering Information, Inc., New York, NY, US; Tee Tong Yan et al.; "Impact life prediction modeling of TFBGA packages under board level drop test" XP002395191 Database accession no. E2004278248902.

* cited by examiner

Figure 9B
TENSILE TEST 2

Figure 9C
FLEXURE TEST

Figure 9A
TENSILE TEST 1

Figure 10

MICRO-IMPACT TESTING APPARATUS

FIELD OF INVENTION

The present invention relates to the field of impact testing microelectronic interconnections, more specifically, to an apparatus for testing the impact properties of said microelectronic interconnections.

BACKGROUND OF THE INVENTION

An ever-increasing number of portable devices, such as mobile telephones, portable media players and portable computers, for example, are now available to consumers. Accordingly, as a device becomes portable, the usage conditions that it is subjected to will vary greatly, such as from a device under static use such as a desktop computer, for example. Portable devices are more likely to experience shocks from impacts and varying thermal operating conditions arising from the different environments in which they may be used. In realization of this, the microelectronics industry has adopted standards to gauge how well the various microelectronic components, such as printed circuit boards (PCB) and their mounted components, fair under such conditions.

An example of said standards is the JEDEC standard (JESD22-B111) which is capable of qualifying the component-board interconnection under impact testing. However, the JEDEC test requires the assembling of the component onto a PCB, a process that is not cost effective when done solely for testing purposes. With respect to testing, the present industry practice of solder ball shearing using a standard ball shear tester is not desirable for at least two reasons. Firstly, the ball shear tester is unable to effectively induce the desired mode of failure testing due to its low shear speed. Secondly, the minute specimen of the solder ball represents a challenge, as its size and geometry prevent accurate characterization of the failure when using standard impact testers such as the Charpy or Izod testers as they lack adequate testing resolution.

In the case of PCB components, Siviour et al. [*Dynamic Properties of Solders and Solder Joints, J. Phys. IV France* 110(2003)] describes an experiment using an Instron loading machine to study the effect of varying strain rates upon the solder joints of PCBs. The solder joint, consisting of a solder ball, is attached to a copper pad on a polymer substrate. In the study, a brass blade struck the solder ball at a given speed and the load required to shear the solder ball was recorded. However, the shear speed peaked at slightly over 1 m/s, meaning that the range of the shear speed achieved in this study was rather limited.

More recently, Date et al. [*Impact Reliability of Solder Joints*, 2004 *Electronic Components and Technology Conference*, 2004], describes a mechanical testing apparatus for solder joints. The mechanical test was carried out using a pendulum impact test in which the pendulum setup allowed the test shear rate to range between 0.1 mm/s-1.4 m/s. The fracture energy of the solder joint was taken to equal to the decrease in kinetic energy of the pendulum after it had struck the solder joint. However, a drawback of the method described by Date et al. is that only the fracture energy is provided and no information on the fracture strength is measured. Furthermore, the accuracy of attributing the (expected) loss of kinetic energy of the pendulum to the fracture energy of the solder joint is questionable, as the change in kinetic energy may have resulted from other losses, such as losses due to the vibration of the pendulum as well as to heat and sound in addition to the energy dissipated upon impacting the solder joint.

Despite the above-mentioned developments, there remains a need for a microelectronics interconnection impact tester that is capable of producing the desired failure testing mode in order to provide quantitative and accurate measurements not only regarding the fracture energy, but also regarding the fracture strength of microelectronics interconnections. It is also desirable to provide an impact tester through which, easily reproducible results on test specimens of minute size and geometry are achievable. Furthermore, it is also desirable to provide a cost-effective tester that is also commercially viable for the microelectronics industry to adopt on a large scale.

In order to solve the above-mentioned problems and fulfill the mentioned needs, an impact tester having the features according to the independent claims is provided according to the present invention.

SUMMARY OF THE INVENTION

According to the invention, the micro-impact testing apparatus for measuring the impact characteristics of a microelectronics specimen exposed to an impact thereon, includes a specimen holder for receiving a specimen to be tested, and an impact device. The impact device includes, according to one aspect of the invention, an impact head, a support member, at least one connecting element and a first flexural spring. The support member is connected to the connecting element such that the first flexural spring is firmly attached with its one end to the support member and with its other end to the connecting element. The impact device also includes a second flexural spring being at least substantially identical to said first flexural spring, wherein the connecting element is connected to the impact head in that the second flexural spring is firmly attached with its one end to the connecting element and with its other end to the impact head. The arrangement of the second flexural spring with respect to the first flexural spring is such that the ends of the first and second flexural springs define, in an unloaded state of the flexural springs, a rectangle.

According to a second aspect of the invention, the micro-impact testing apparatus for measuring the impact characteristics of a microelectronics specimen exposed to an impact includes a specimen holder for receiving a specimen to be tested, and an impact device. The impact device includes an impact head, a support member and at least a first flexural spring being attached with its one end to the support member and with its other end to a first side of the impact head. The impact device also includes at least a second flexural spring being at least substantially identical to said first flexural spring and being attached with its one end to the support member and with its other end to a second side of the impact head, said second side being opposite to said first side thereof.

DETAILED DESCRIPTION OF THE INVENTION

The impact head, according to the above embodiment of the impact testing apparatus, is moveable transversally with respect to the first and second flexural springs along a linear line between a spring-loaded position (loaded position) and an impact position thereof. Further, the specimen holder is aligned with the impact device such that the test specimen received in said test specimen holder is arranged in said impact position of the impact head. This enables the impact head to precisely impact the specimen after traveling from its loaded position towards its impact position along said linear line. The linear motion is important in order for the impact head to provide for the required precise shear force to the test specimen upon release. The linear motion of the impact head is also necessary to enable the testing apparatus to carry out tests on test specimens of minute size and geometry.

In addition, further advantages of using the above-mentioned arrangement, including the flexural spring, are that said flexural springs are frictionless, provide for a vibration-free linear motion of the impact head and are of high stiffness when placed in a perpendicular arrangement with respect to the support member.

With regard to the above-mentioned embodiment, it is to be noted that it may not always be necessary to form the rectangle defined by the ends of the first and second springs. Should the lengths of parallel corresponding springs vary from each other, the same linear effect, i.e. a precise linear motion of the impact head, may still be achieved by varying the spring characteristics, such as the stiffness, for example.

In a further embodiment of the invention, the micro-impact testing apparatus, as described above, further includes a third and a fourth flexural spring, which are at least substantially identical to said first flexural and second flexural springs. The third and the fourth flexural springs are connected to the support member, the connecting element and the impact head, respectively, in the same manner as the first and the second flexural springs.

In an alternative embodiment, the above described micro-impact testing apparatus includes only a third flexural spring. In this embodiment, one end of the third flexural spring is connected to the support member and the other end of the flexural spring is connected to the connecting element in the same manner as the first flexural spring. The ends of the first and the second flexural springs define a rectangle on one side of the second flexural spring, and the ends of the second and the third flexural springs define a rectangle on an opposite side of the second flexural spring. The characteristics of the flexural springs are designed so as to ensure that the impact head is moveable along said linear line. In any of the above-mentioned embodiments, the flexural springs may be arranged together on one side of the impact head in an at least substantially overlapping relationship with respect to each other. In other words, when seen in the traveling direction of the impact head (top view), the flexural springs will appear as at least substantially overlapping each other. In the above embodiment, where flexural springs of the micro-impact testing apparatus are arranged on one side of the impact head in an at least substantially overlapping relationship with respect to each other, the flexural springs may be connected to a single connecting element.

However, in further exemplary embodiments of the invention, the apparatus may further comprise a second set of flexural springs. Each flexural spring of the second set of flexural springs is at least substantially identical to said first flexural spring. The second set of flexural springs is connected to another connecting element on a substantially opposite side of the impact head. As mentioned above, the flexural springs of said second set of flexural springs, on the opposite side of the impact head, are arranged in an at least substantially overlapping relationship with respect to each other, when seen in the traveling direction of the impact head. In these embodiments of the invention, the arrangement of the flexural springs on either side of the impact head may advantageously be symmetrical to said linear line. In other words, the arrangement of the second set of flexural springs substantially mirrors that of the first set of flexural springs.

In this respect, it should be noted that the term "substantially opposite" may be taken to mean that the first and second sets of springs may be, as mentioned, mirror images, i.e. placed 180 degrees part. However, the term may also be taken to mean that the two sets of springs are separated by a given angle resulting in a radial relationship between the two sets of springs, with the impact head acting as the origin when seen in the direction of the said linear motion.

Alternatively, in the embodiments where two sets of springs connect the impact head to respective connecting elements on either side of the same, the arrangement of the springs on the opposite sides may be asymmetrical as well.

At this juncture, it should be noted that in any of the preceding embodiments, or those that follow, the term flexural spring refers to the manner in which the spring functions with regard to the present apparatus, i.e. via a linear directional oscillation along a single line. The linear motion of the flexural spring is to be uni-directional along said single line, with the flexural spring moving linearly along said direction upon release from the loaded position (flexed state) to the unloaded position (not flexed state).

Accordingly, the flexural spring may be, but is not limited to, a flat (monolithic) spring, a leaf spring or a notch spring. A notch spring may be a flat spring that has a wedge-like feature or a segment excision feature along its peripheral edge, for example. When the notch spring undergoes flexure, the wedge-like section may either expand or contract into a biased state only to return to its original state upon release. The meaning of a flexural spring is also extended to include a flexible beam, for example, that satisfies the elasticity requirements of the impact head of the impact testing apparatus according to the present invention.

The impact head of the above-mentioned embodiments of the micro-impact testing apparatus includes a load element, a core rod, a load cell, and a striker head. The load cell, the load element and the striker head may be connected to each other by the core rod in a co-axial arrangement, such that said arrangement extends along the linear displacement line that the impact head is slated to travel along.

The striker head in the above-mentioned embodiments is adapted to apply a shear force on the microelectronics test specimen upon impact. In additional embodiments, the striker head may also be adapted to apply other directional forces to simulate different modes of failure. In this regard, apart from the application of a shear force, the striker head may also apply a tensile force (for a tensile strength test) or induce a bending moment (for a flexure test) on the test specimen if adapted and applied appropriately, for example.

According to a further embodiment of the invention, the support member is provided with a through-hole therein, wherein the core rod extends through and protrudes vertically outwardly from said through-hole. The protruding end of the core rod includes a plunger to aid in the (where applicable) manual movement of the core rod. The core rod may be further supported by a compression spring or a tension spring, wherein the compression/tension spring is coaxially mounted on the portion of the core rod within said through-hole such that one end of the spring is attached to the support member and the other end of the spring is attached to the core rod.

The compression spring may be actuated by a cylindrical collar. The radius of the cylindrical collar is larger than that of the core rod and allows for, at the very most, sliding contact between the inner wall portion of the through-hole and the cylindrical collar. The cylindrical collar is arranged to abut the top of the impact head and co-axial to the core rod, such that when the core rod is raised it passes through said through-hole up to the point when it contacts the fixed compression spring. After contacting the compression spring, any further displacement of the core rod results in the cylindrical collar compressing the compression spring Such a compression or tension spring is provided in this embodiment of the invention in order to further increase the speed of the striking head when it is released from its loaded position.

During the loading process, the entire impact head, including the striker head, load cell and load element, is translated along the said linear line by means of the core rod. During the translation, the flexural springs that are attached to the impact head become biased to returning the impact head back to the original equilibrium position. In embodiments where additional acceleration is required (said additional acceleration is provided by including additional potential energy), the previously mentioned compression or tension spring may be included as follows.

For example, as mentioned in the above embodiment including a compression spring, as the impact head enters a loaded position, the cylindrical collar arranged coaxially on the core rod begins to compress the compression spring thereby creating a further avenue of potential energy that may be converted to kinetic energy upon release of the impact head.

The load cell sensor is a transducer, which converts force into a measurable electrical output. Although there are many varieties of load cells, a compression load cell may be used in the present apparatus. However, in place of the compression load cell, various force transducers may be used such as piezoelectric transducers and strain gauges, for example. In this respect, depending upon the type of force-measuring device used, said sensor may be situated either directly on the impact head or otherwise.

In another embodiment, the micro-impact testing apparatus further includes a linear variable displacement transformer (LVDT) sensor. The LVDT sensor is embedded in the support member. It is arranged to be cylindrically attached to the inner-wall portion of the through-hole and coaxially aligned with the through-hole of the support member. As such, the core rod may be, at the very most, in sliding contact with the inner surface of the LVDT sensor. The LVDT sensor provides displacement data with regard to the core rod, which in turn can be used to determine the velocity and acceleration of the impact head assembly.

LVDTs typically consist of a primary magnetic coil, a secondary magnetic coil and a plunger that rides on the object (core rod) whose position is being measured. In the present apparatus, the displacement of the core rod causes the mutual inductance of the secondary coil to vary relative to the primary coil, and thus the relative voltage induced from the primary coil to the secondary coil will vary as well. This allows the displacement of the core rod (and the attached impact head assembly) to be measured accurately. Apart from using LVDTs to measure the displacement of the core rod, magneto resistive, optical triangulation, photoelectric, position displacement, ultrasonic, and variable resistance technology sensors may also be used, for example.

In a further embodiment of the invention, the micro-impact testing apparatus further includes a speed control block mounted atop of the support member by means of a guide element. The precise location of the speed control block is such that it lies substantially along the same linear line of motion as that of the core rod (and hence, the impact head as well). The speed control block has an attachment means to attach, in a releasable manner, to the portion of the core rod that protrudes outwardly from the through-hole of the support member, specifically, to the plunger located atop. This allows the speed control block to engage the top protruding portion of the core rod, thereby holding the core rod and the entire impact head assembly in the loaded position until it is ready to be released to reach the impact position. The top of the protruding portion of the core rod, as previously mentioned may include a plunger. Said plunger functions to aid in the attachment and detachment of the core rod from the speed control block when the impact head is in the loading position.

The guide element provides for an adjustment of the speed control block along the said linear line, and therefore, adjusts the extent of the deformation of the flexural springs in connection with the impact head. This in turn varies the potential energy of the impact head assembly. The guide element used may be a slide rail or a slot system, as long as it permits the speed control block to be moveable along said linear line.

In the embodiment including the speed control module, the attachment means may be, but is not limited to, a mechanical screw, a clamping device or a magnet. The magnet may be in the form of an electromagnet that is activated and deactivated by the switching on and off, respectively, of an electrical current.

All of the preceding embodiments include a specimen holder for the present apparatus. The specimen holder includes a specimen-clamping device, a mounting plate and a three-dimensionally translatable stage. The mounting plate is mounted onto the translatable stage. Atop of the mounting plate, the specimen-clamping device, for clamping a test specimen, is affixed. The position of the stage (and therefore the clamp) is accurately adjustable in the X, Y and Z-axes by means of three micrometers, one for each of the X, Y and Z directions. It may be also possible to adjust the angle of impact upon the test specimen by including a specimen—clamping device that rotates about a given angle θ.

In a further embodiment of the invention, the specimen holder of the micro-impact testing apparatus further includes a microscope or a charge coupled device (CCD) video camera or a combination thereof. The microscope allows for monitoring and checking the precise positioning of very small test specimens in the specimen holder in order to allow an exact impact location to be struck.

In yet another embodiment of the micro-impact testing apparatus, said apparatus further includes a test specimen temperature variation device. The test specimen temperature-varying device may be adapted to vary the temperature of the environment surrounding the test specimen in a broad range, for example in the range of −40° C. to 100° C.

As mentioned above, according to the second aspect of the invention, the micro-impact testing apparatus for measuring the impact characteristics of a microelectronics specimen exposed to an impact includes a specimen holder, for receiving a specimen to be tested, and an impact device. The impact device includes an impact head, a support member and at least a first flexural spring being attached with its one end to the support member and with its other end to a first side of the impact head. The impact device also includes at least a second flexural spring being at least substantially identical to said first flexural spring and being attached with its one end to the support member and with its other end to a second side of the impact head, said second side being substantially opposite to said first side thereof.

The impact head, according to this aspect of the invention, is moveable transversally with respect to the flexural springs along a linear line between a spring-loaded position and an impact position. The specimen holder is aligned with the impact device such that the specimen is arranged in said impact position of the impact head so that the impact head is capable of impacting on the specimen after traveling from its loaded position towards its impact position along said linear line upon release.

According to a further embodiment of this aspect of the invention, the apparatus may further include an additional even number of substantially identical flexural springs. The even number of flexural springs are connected to the respective structural elements of the apparatus in the same manner as those of the first and second flexural springs, such that equal numbers of flexural springs are attached on either side of the impact head.

In an exemplary embodiment, the flexural springs may be arranged on either side of the impact head in a side-by-side manner, i.e. the springs may lie in a single plane. Alternatively, the flexural springs on either side of the impact head may be arranged in an at least substantially overlapping relationship with each other, when seen in the traveling direction of the impact head.

It should be further noted that in order to allow a movement of the impact head along said linear line, the flexural springs of the micro-impact testing apparatus, according to the above described second aspect of the invention, should either have some elasticity in their longitudinal direction. Alternatively, the flexural springs may be attached to the support member and/or to the impact head to ensure that the change in the length of the flexural springs, which occurs when flexing the same, is accounted for. This may be achieved, for example, where the impact head contains a recess in which the flexural springs are slideably supported.

In general, it should further be noted that one essential feature of the invention is to provide for a micro-impact testing apparatus in which the impact head is suspended by means of flexural springs in such a manner that a precise linear movement of the impact head between its spring-loaded position and its impact position is ensured. Although different specific embodiments of the micro-impact testing apparatus according to the invention have been described so far, it should be understood that other embodiments fulfilling the above requirement should also fall within the scope and spirit of the present invention.

As an example, the flexural springs described in connection with the first aspect of the invention may not necessarily be identical. For example, one flexural spring may be longer that another one. The characteristics regarding the flexural springs should be such that they are mutually designed to ensure said linear movement of the impact head by the suspension system formed by all flexural springs used in a certain embodiment of the invention.

It should also be noted that all the above-mentioned and following embodiments may be arranged either in a vertical or horizontal manner. A vertical arrangement would be one wherein the effect of gravity is utilized as the impact head translates from a position of higher gravitational potential energy to that of a lower gravitational potential energy. In a horizontal arrangement, gravity does not come into play, but the potential energy needed is generated solely due to the effect of the flexural springs and, where applicable, in combination with additional compression (or torsion) springs.

The following accompanying drawings, and detailed description of the invention, as well as examples of the embodiments, will further aid in the understanding of the micro-impact testing apparatus and its various embodiments according to the present invention. However, said drawings and embodiments should not be construed as limiting the present invention to the illustrated embodiments.

In the following, examples of the various embodiments of the invention are described including references to the accompanying figures.

Figure 1:
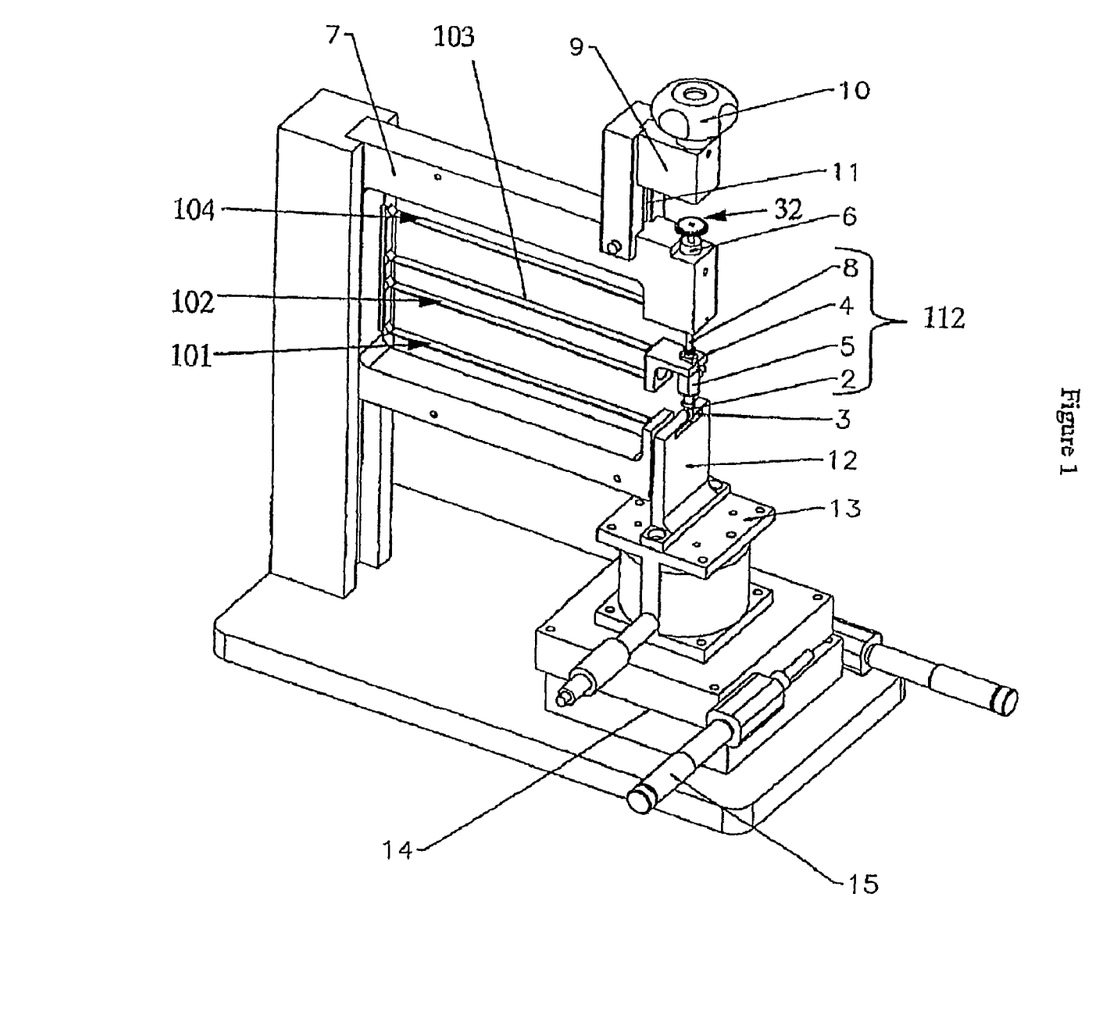
FIG. 1 shows a perspective view of a micro-impact testing apparatus according to the invention, including a specimen holder, a C-shaped support member and a impact head assembly.

FIG. 1 shows a perspective view of the micro-impact testing apparatus according to the invention, including a specimen holder 12,13,14 and 15, a C-shaped support member 7 and an impact head 112. The impact head includes a striker head 2, a load cell 5, a load element 4 arid a core rod 8. Mounted atop of the assembly 112, specifically, on the core rod, is a plunger 32, which is present in all embodiments that follow.

The embodiment also includes four flexural springs 101, 102, 103 and 104 for generating the impact energy of the moving components, i.e. the impact head 112. A speed control block 9 is mounted atop the C-shaped support member 7 and serves to hold the plunger 32 in place during the loading of the apparatus. Subsequently, the speed control block 9 is able to release the plunger 32, and therefore, the impact head assembly 112 as well. The height of the speed control block 9 above the support member 7 is adjustable by means of a sliding guide 11. The speed control block 9 includes an attachment mechanism 10 capable of securing the plunger 32, and later releasing the same. The mounting of the speed control block 9 on the sliding guide 11 allows for the variation of deformation that the flexural springs 101, 102, 103 and 104 undergo to be controlled via the height of the speed control block 9. The varying height of said speed control block 9 corresponds to the variance in potential energy as provided by the flexural springs 101, 102, 103 and 104 prior to the release of the impact head assembly 112.

As mentioned above, the embodiment of FIG. 1 also includes the specimen holder 12,13,14 and 15. The specimen holder 12,13,14 and 15 includes a stage 14, a specimen-clamping device 12, a mounting plate 13 and three micrometers. The stage 14 is movable in three axes for specimen position adjustment. The specimen-clamping device 12 is mounted firmly onto the mounting plate 13. The mounting plate 13 is in turn mounted onto the stage 14. The position of the stage 14 is accurately adjustable by the three micrometers 15 in the X, Y and Z directions.

It may be also possible to adjust the angle of impact upon the specimen by including a specimen holder that may be able to rotate about a given angle θ. In further exemplary embodiments, a microscope (not shown) may be included for precise specimen alignment. In such an embodiment, the microscope may be positioned to monitor the alignment in two directions, one from the front of the apparatus (i.e. along the length of the flexural spring) and/or from the side (i.e. along the width of the flexural spring).

Figure 2:
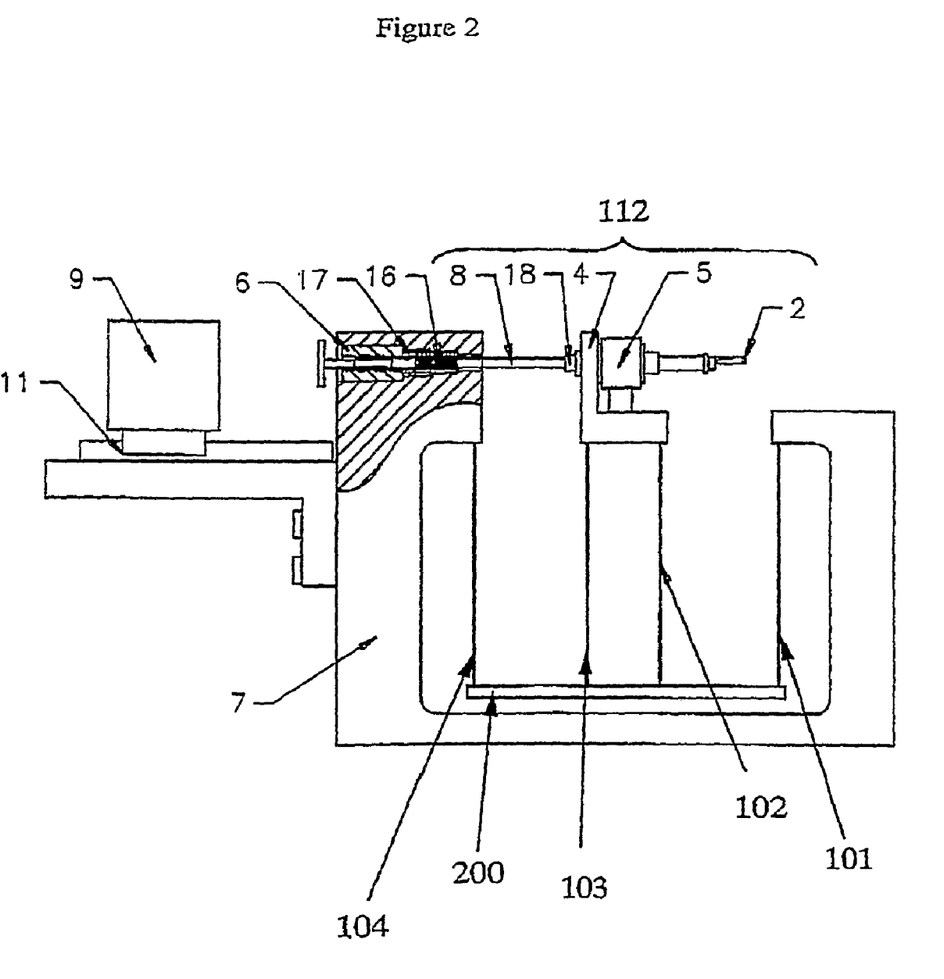
FIG. 2 shows a side view of an exemplary embodiment of FIG. 1, wherein the impact head is connected indirectly to the C-shaped support member by means of a connecting element.

FIG. 2 shows a side view of one exemplary embodiment of the invention, wherein the impact head 112 is connected, indirectly, to the C-shaped support member 7 by means of a connecting element 200. The flexural springs 102 and 103 connect one side of the impact head to the connecting element 200. As mentioned above, the striking speed of the impact head assembly 112 is primarily controlled by the flexural springs 101, 102, 103 and 104.

During the loading process, as mentioned above, the impact head assembly 112 is displaced towards the speed control block 9. During the displacement of the impact head assembly 112 and subsequent attachment of the plunger 32 to the speed control block 9, the flexural springs 102 and 103 are deflected in the direction of the displacement. Accordingly, the deflection of flexural springs 102 and 103 causes the impact head 112 to translate upwards and inwards towards the connecting element 200 (i.e. inwards along the length of the flexural springs). Accordingly, the connecting element 200 also travels in the direction of the above-mentioned displacement of the impact head 112. The corresponding upward deflection of the flexural springs 101 and 104 results in the connecting element 200 to translate towards the impact head 112 (i.e. outwards along the length of the said flexural springs).

Hence, the outward translation of the connecting element 200 and the inward translation of the impact head 112 (where said translations occur at equal rates) results in a compensatory effect that maintains the impact head 112 in a single plane (in a straight line) as it moves upwardly between the neutral equilibrium position (unloaded state) to the loaded position.

The striking speed of the impact head 112 may also be increased by the insertion of a compression spring 16 into the through-hole of the C-shaped support member 7 as shown. In the figure, the compression spring 16 is mounted coaxially to the core rod 8. The core rod 8 may be in sliding contact with said compression spring 16. The preloading of the compression spring 16 may be adjusted by a screw block 17. When the impact head assembly 112 moves toward the speed control block 9, the compression spring 16 is compressed by a cylindrical collar 18, which is mounted co-axially with the core rod 8 and may be present in earlier and subsequent embodiments to function as described here. The additional potential energy generated by the compression spring 16 is added to the potential energy already available to the impact head 112. Upon release, the additional potential energy generated by the compression spring 16 will be converted into kinetic energy, thereby sending the striking head 2 along a linear path to impact the solder joint specimen under test.

The C-shaped support member 7 of the present embodiment also includes a through-hole in which a LVDT sensor 6 is arranged. The above-mentioned arrangement of the compression spring 16, the screw block 17 and the core rod 8 is carried out within said through-hole. The core rod 8 passes through the compression spring 16 and a LVDT sensor 6 arranged within the through-hole in a coaxial arrangement with a portion of the core rod 8 protruding from the top of the through-hole. Approximately halfway in the through-hole, a constriction feature, whereby said constriction is a step-feature of reduced diameter, is present. The portion of the through-hole with a reduced diameter (which is located nearer to the opening on the side of the speed control block 9) is sufficient for the core rod to be, at the very most, in sliding contact with the LVDT sensor 6. The LVDT sensor 6 is positioned along the inner wall of said reduced diameter portion of the through-hole and may be, at the very most, in sliding contact with the core rod 8.

Figure 3:
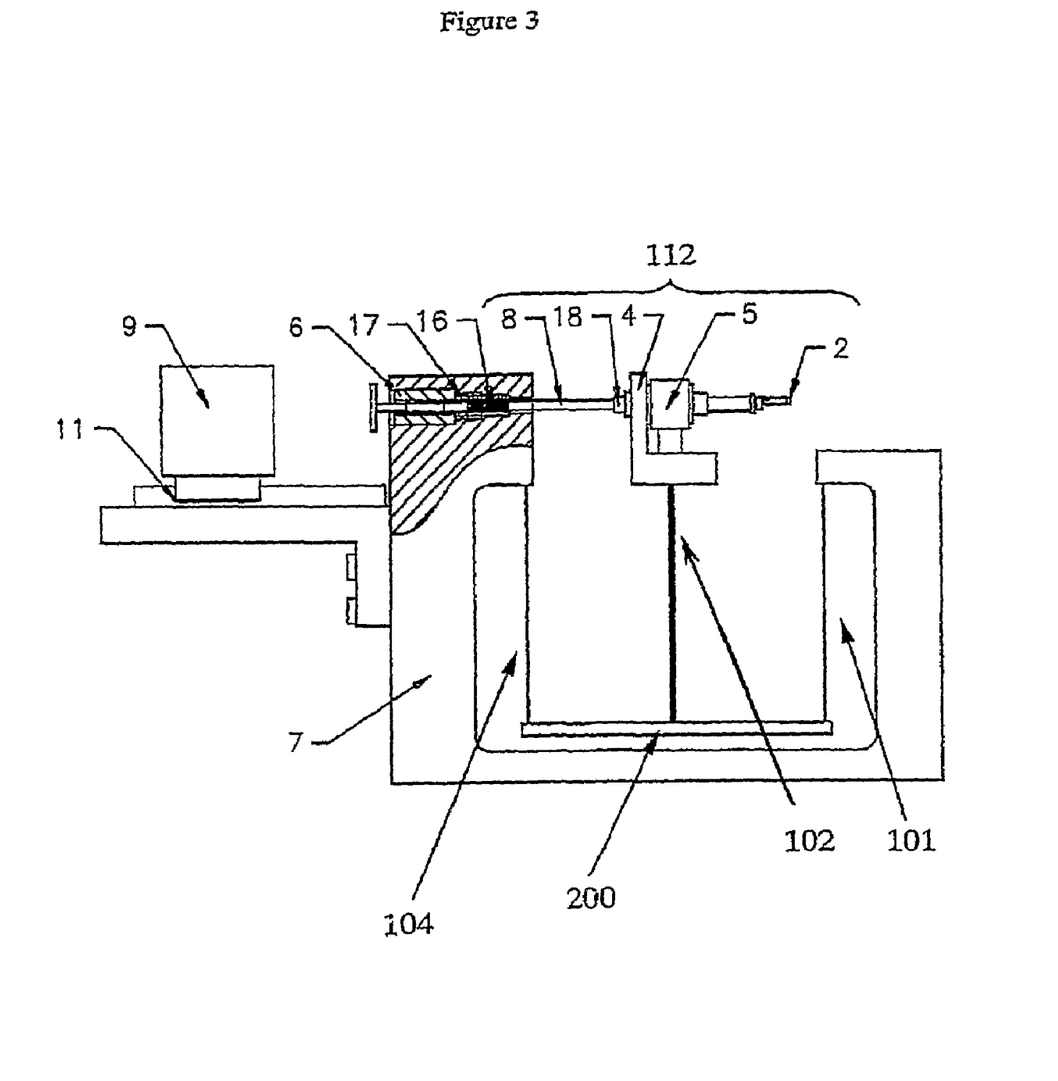
FIG. 3 shows a side view of another exemplary embodiment of FIG. 2, wherein the impact head is connected directly to the connecting element by a single flexural spring.

FIG. 3 shows a side view of another exemplary embodiment of FIG. 2 wherein the impact head assembly 112 is connected directly connected to the connecting element 200 by a single flexural spring 102. The C-shaped support member 7 generally has inwardly bending portions at the free ends of the C-shape. The extent of bending of the said inwardly bending portions, as shown in the embodiments, is substantially equivalent, but is not limited, to that of a right angle. It is at these inwardly bending portions that one end of the flexural springs 101 & 104 connect to the C-shaped support member 7 and with the other end connected to the connecting element 200. The flexural springs 101 & 104 are connected in a similar manner such that said flexural springs are parallel to each other. The arrangement of the third flexural spring 103 is also parallel to the aforementioned springs 101 & 104. With regard to the length of the three flexural spring 101, 103 & 104, in this particular embodiment, they are of equal length. However, as mentioned above, the length of each spring may vary according to the stiffness characteristics of each individual spring provided that the end result is that the impact head 112 moves in the previously described linear manner.

The motion of the present embodiment is essentially similar to that as described above. As the impact head 112 is raised to the loading position, the impact head 112 would tend to move in an arc whereby the distance between the assembly 112 and the connecting element decreases. This movement occurs as the spring 102 flexes upwards and bends towards the upper horizontal portion of the C-shaped support member 7.

However, the raising of the impact head 112 also simultaneously causes the connecting element 200 to be raised as well. Due to the upward motion of the connecting element 200, the springs 104 and 102 also flex upwards, causing the connecting element 200 and the indirectly attached impact head 112 to translate outwards, as described above.

Therefore, although the distance of the impact head 112 with respect to the connecting element 200 decreases during the upward motion, the distance of the connecting element 200 with respect to the vertical section of the C-shaped support frame 7 increases simultaneously, i.e. the connecting element moves outwards. The combination of the two movements cancel out each other and results in the impact head assembly 112 being maintained within a single vertical plane. Accordingly, the movement of the assembly 112 is linear as well as the said assembly translates between the loading position to the impact position.

Figure 4:
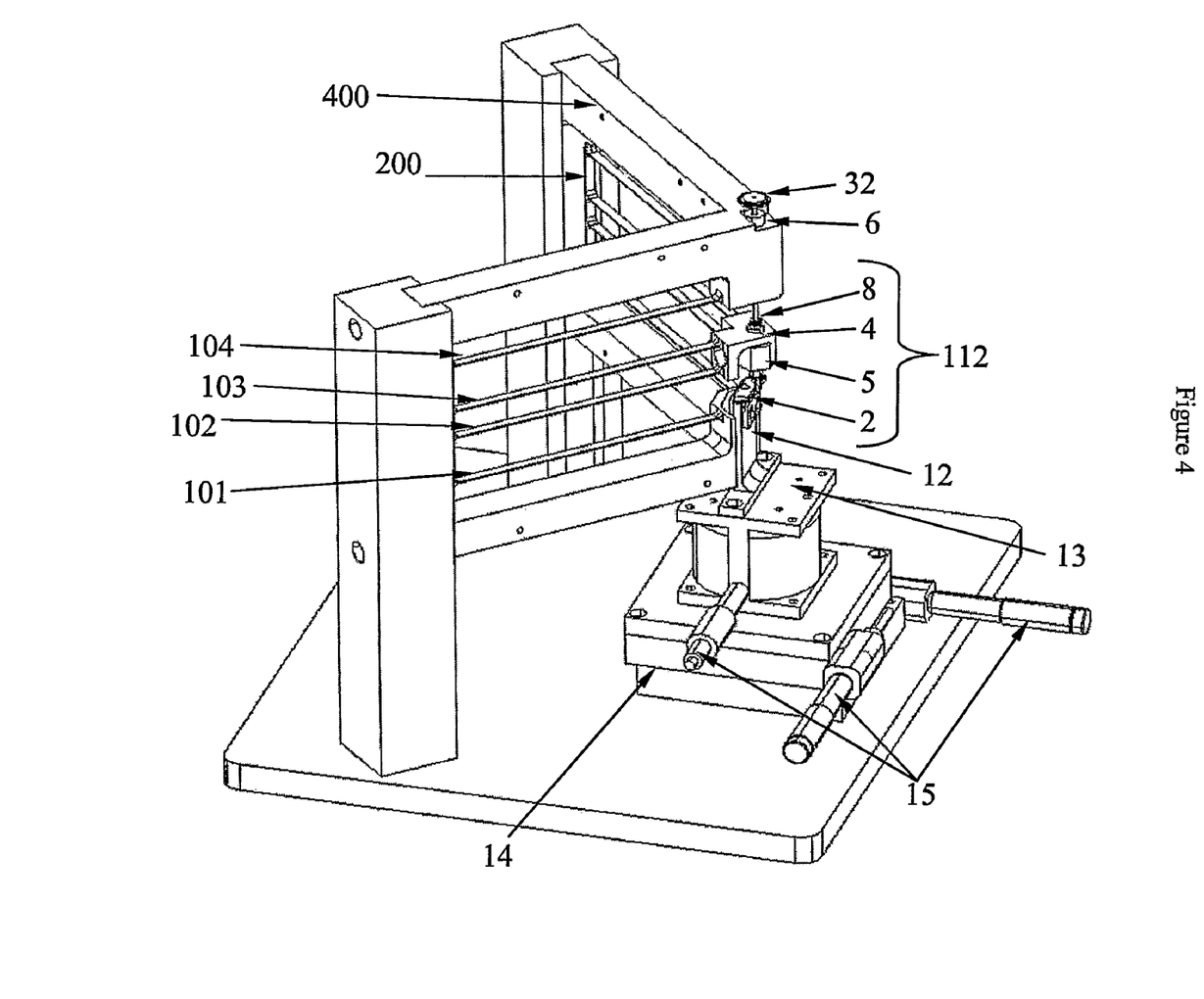
FIG. 4 is an illustration of a further embodiment of the impact testing apparatus wherein the flexural springs connect the impact head to an angled support member.

FIG. 4 is an illustration of a further embodiment of the impact testing apparatus wherein the four pairs of flexural springs 101, 102, 103 & 104 connect, on opposite side of the impact head assembly 112, to an angled support member 400. The angled support member 400 may be essentially thought of as two C-shaped support members linked either together or as an inverted U-shaped support member 30 that is bent laterally about a central axis to form a v-shape, if viewed from the top-plan view, for example. The angle of the v-shape shown in embodiment of FIG. 4 is that of a right angle (90 degrees). However, in further embodiments, the angle may be varied anywhere between the range of 0 degrees to 180 degrees.

Each pair of flexural springs 101, 102, 103 and 104 lie within their respective horizontal planes, i.e. at least two flexural springs per plane, arranged on either side of the assembly 112. In other words, the arrangement of the flexural springs on the opposite side of the assembly 112 may essentially be a mirror image of the first set of flexural springs. The flexural spring pairs 102 & 103, for example, are attached to the load element 4 of the impact head assembly 112. The remaining pairs of flexural springs connect the connecting element 200 to the angled supporting member 400.

Figure 5:
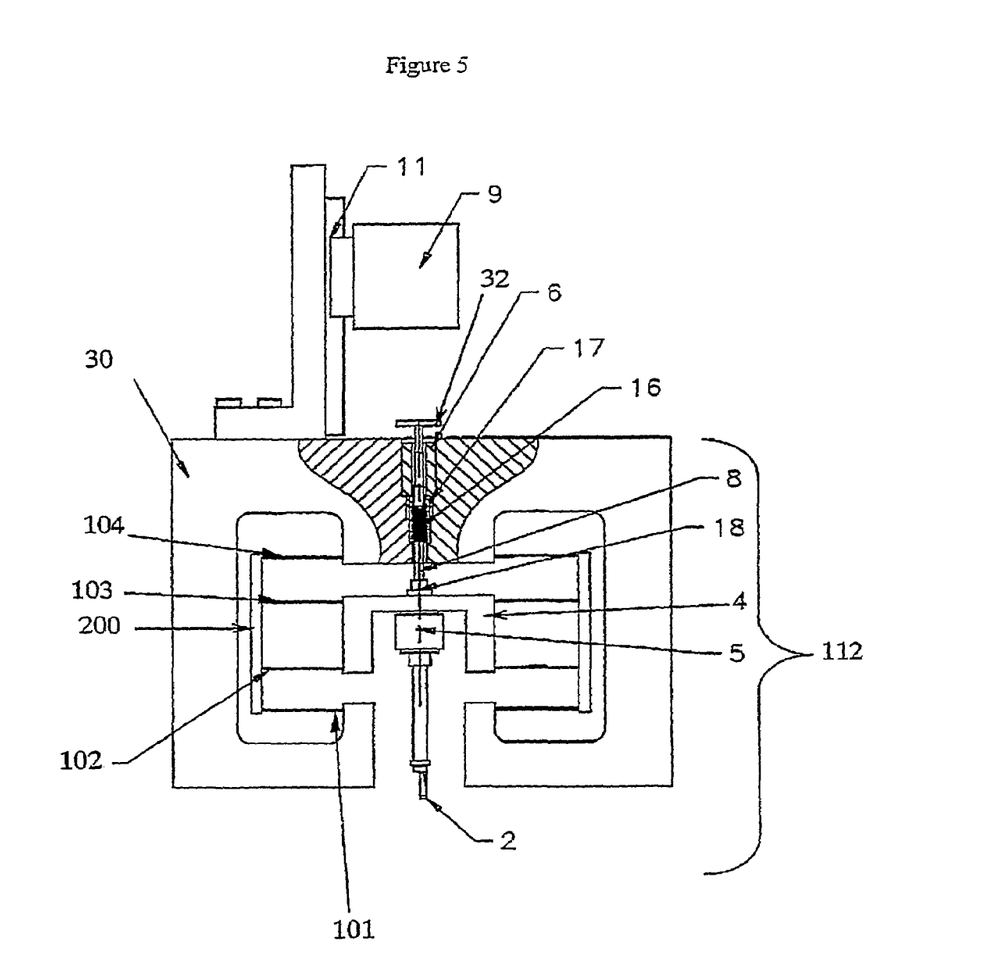
FIG. 5 is a further exemplary embodiment of that as shown in FIG. 4, where both sides of the impact head are connected via flexural springs that are 180° apart, indirectly to an inverted U-shaped support member in a symmetrical manner via the connecting element.

FIG. 5 illustrates a further exemplary embodiment of the first aspect of the present invention. In this exemplary embodiment, the opposite sides of the impact head 112 are connected indirectly to an inverted U-shape support member 30 via two connecting elements 200. In this exemplary embodiment, the impact head includes the load element 4, the load cell 5, the striking head 2 and the core rod 8. The two opposite ends of the load element 4 are attached via four pairs of flexural springs 101, 102, 103 & 104 to both connecting elements 200, located on opposite sides of the impact head assembly 112. The arrangement of the flexural springs 102 & 103 to the load element is the same as that in FIGS. 1 and 2. The connecting elements 200 are connected to the inverted U-shaped support member 30 via the additional two pairs of flexural springs 101 & 104. The arrangement and alignment of the pairs of flexural springs 101, 102, 103 & 104 and connecting elements 200, in relation to the impact head, is such that the flexural springs 101, 102, 103 & 104 and the connecting elements 200 are symmetrical about the path of linear displacement. Essentially, the arrangement of the flexural springs in the aforesaid embodiment may be on either side of the impact head, in a directly opposite manner or at angle to each other.

During the loading of the impact head assembly 112, the core rod 8 will be displaced upwards thereby causing flexural springs 102 and 103 to be deflected towards the speed control block 9. The speed control block 9 may attach to the impact head assembly in two ways. Firstly, the speed control block 9 may be adjusted along the sliding guide 11 to reach the plunger 32, or alternatively, in a second instance, the plunger 32 is pulled up towards the speed control block 9. In either method, upon the plunger 32 reaching the speed control block 9, the attachment means 10 may be utilized to secure the plunger 32 at said predetermined height until subsequent release. The effect of the connecting element in the present embodiment is the same as described above. Should the core rod be sufficiently displaced towards the speed control block 9, and should the screw block 17 allow for any pre-loading of the compression spring 16, the cylindrical collar 18 will further act to compress the compression spring 16 to provide additional potential energy to the impact head assembly 112.

Figure 6:
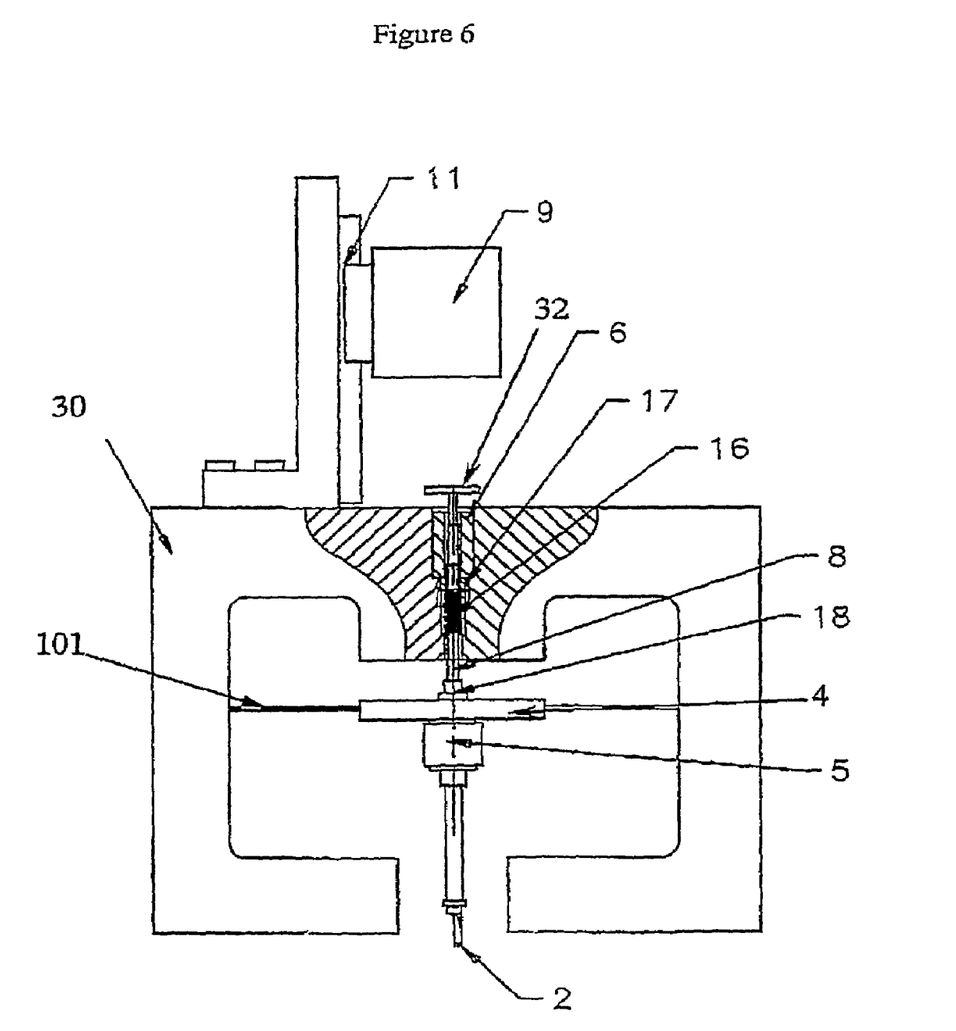
FIG. 6 is an embodiment of the second aspect of the present invention having two flexural springs, each with one end attached to opposite sides of the impact head, and the other end attached directly to the inverted U-shaped support member.

FIG. 6 is a side view of an illustration of an embodiment of the second aspect of the impact testing apparatus wherein the opposite sides of the impact head assembly 112 are directly connected to the inverted U-shaped support member 30. As in the previous embodiments shown in FIGS. 1-5, the alignment of the impact head assembly 112, the core rod 8 and the attachment/detachment means of the speed control block 9 are vertical and collinear. In this exemplary embodiment, the load element 4 is attached to the inverted U-shaped support member 30 directly via the pair of flexural springs 101. The flexural springs 101 are attached to the load element 4 in a non-rigid sliding manner such that when the impact head 112 is being loaded, an end portion of the flexural springs 101 slides within the load element 4. In other words, the load element 4 may have a small recess within which said end portion of the flexural spring is arranged to be able to slide, for example.

Alternatively, the flexural spring 101 may be of such a material that permits for a certain degree of elastic strain to be present. In other words, the flexural spring 101, apart from being elastic in the lateral direction (widthwise), may also be elastic in the longitudinal direction (lengthwise).

Figure 7:
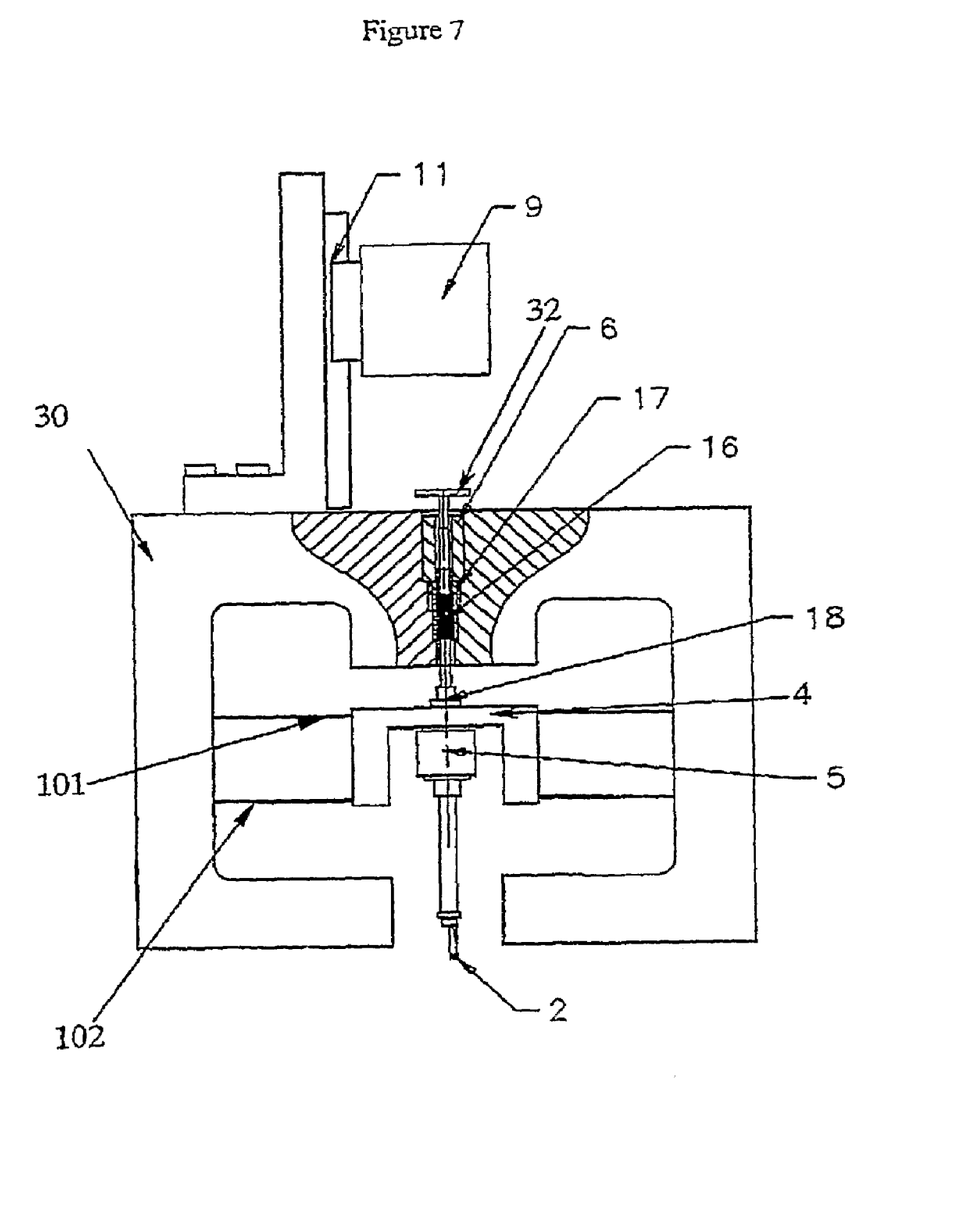
FIG. 7 is a side view of an illustration of the second aspect of the present invention, as shown in FIG. 6, with the exception that two pairs of springs are instead to directly connect the inverted U-shaped support member to the impact head.

FIG. 7 is a side view of a further embodiment of FIG. 6 having two pairs of flexural springs 101, 102, each with one end attached to opposite sides of the impact head, and the other end directly to the inverted U-shaped support member 30. As described above, the loading process remains the same as the embodiment described in FIG. 6. The feature that differentiates the embodiment of FIG. 6 from that of FIG. 7 is the presence of an additional pair of flexural springs 102 to connect the load element 4 to the inverted U-shaped support member 30. The additional flexural springs 102 are attached to the load element 4 in a parallel manner similar to that of the first pair of flexural springs 101.

Figure 8:
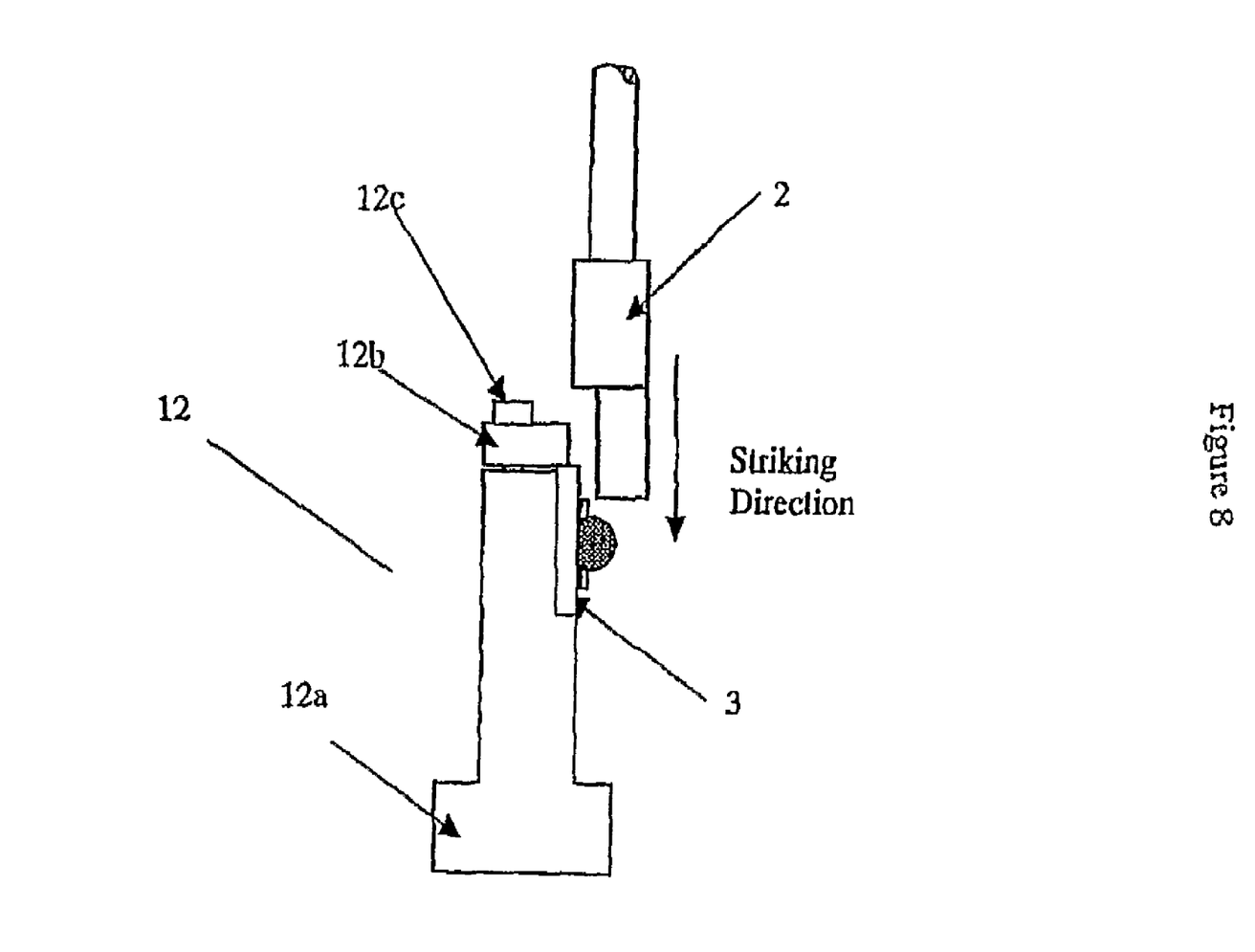
FIG. 8 illustrates a test specimen (solder joint) prior to being struck by the impact head during impact testing.

FIG. 8 illustrates the striking of a solder joint by the striking head 2 during impact testing. The specimen fixture assembly includes a base fixture block 12a and a clamping component 12b. The test specimen 3 may be fixed and secured by the screw 12c. As the striking head 2 translates linearly in the direction indicated in FIG. 7, a shear force will be exerted in the same direction on the test specimen 3.

Figure 9A:
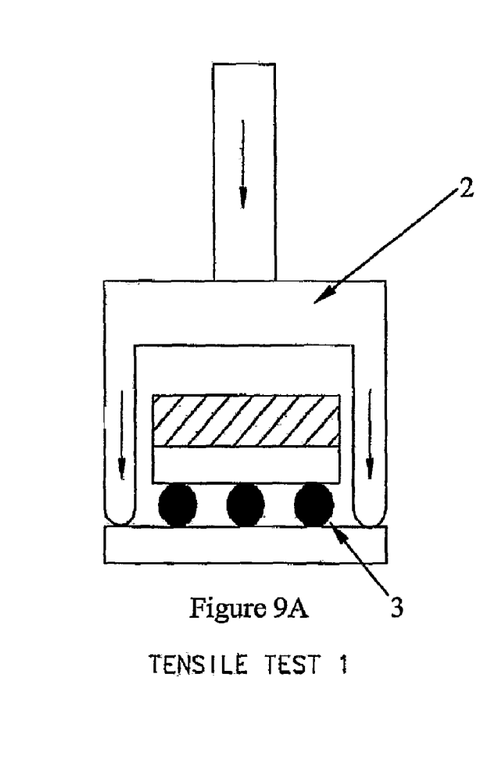
FIG. 9A-9C are illustrations of possible arrangements and adaptations of the substrate and striking head respectively to simulate various modes of failure.
Figure 9B:
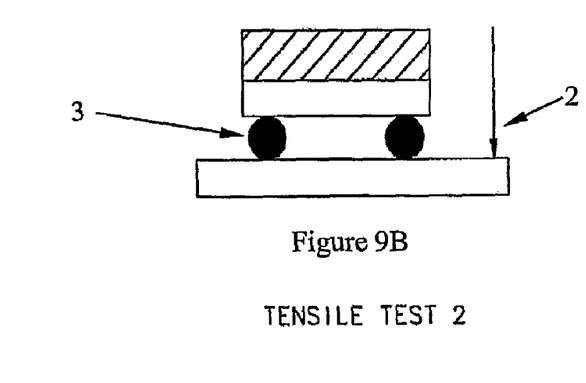
Figure 9C:
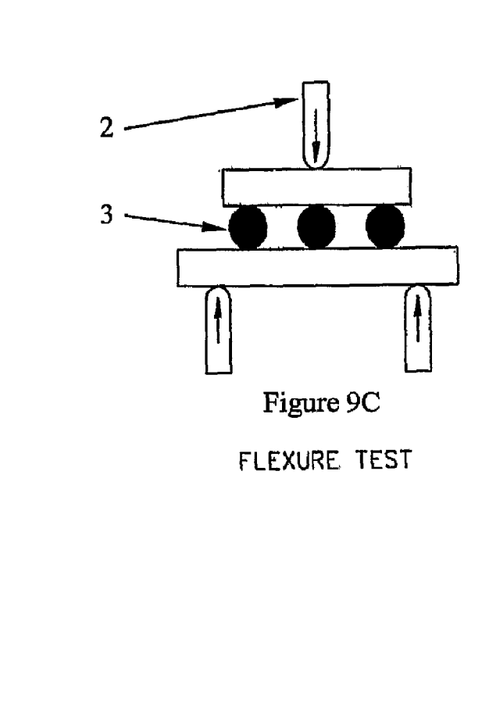

FIG. 9A-9C are illustrations of possible arrangements and adaptations of the substrate and striking head respectively to simulate various modes of failure. FIG. 9A shows how the striking head 2, in further embodiments, may be adapted to test the strength of a test specimen 3 when subjected to a tensile force. In the illustrated embodiment, the striking head 2 includes two arms extending outward about a common line of symmetry. The test specimen (solder ball) 3 shown is such that is connects two substrates and the impact is directed by both arms of the striking head 2 against the lower substrate with the top one being fixed. This causes the test specimen 3 to undergo a uniform state of tension before failure occurs.

FIG. 9B is a further exemplary embodiment of how a tensile test may be implemented. In this particular embodiment, the impact force is applied to one side of the lower substrate. Accordingly, the striking member in this embodiment (not shown) would not require two arms as in the previous embodiment.

FIG. 9C is an example of the implementation of a flexure test using the impact testing apparatus of the present invention. In this embodiment, the striking head 2 applies a force on the top substrate. Simultaneously, the bottom substrate also has at least two forces applied such that the direction of the force on the top substrate passes in between the direction of the two forces applied on the bottom substrate. Accordingly, this results in causing the substrates to which the test specimens 3 are affixed to, to flex. The striking head as used in the embodiment of FIG. 9A may be used to impact the bottom substrate when implementing the aforesaid flexure test.

Figure 10:
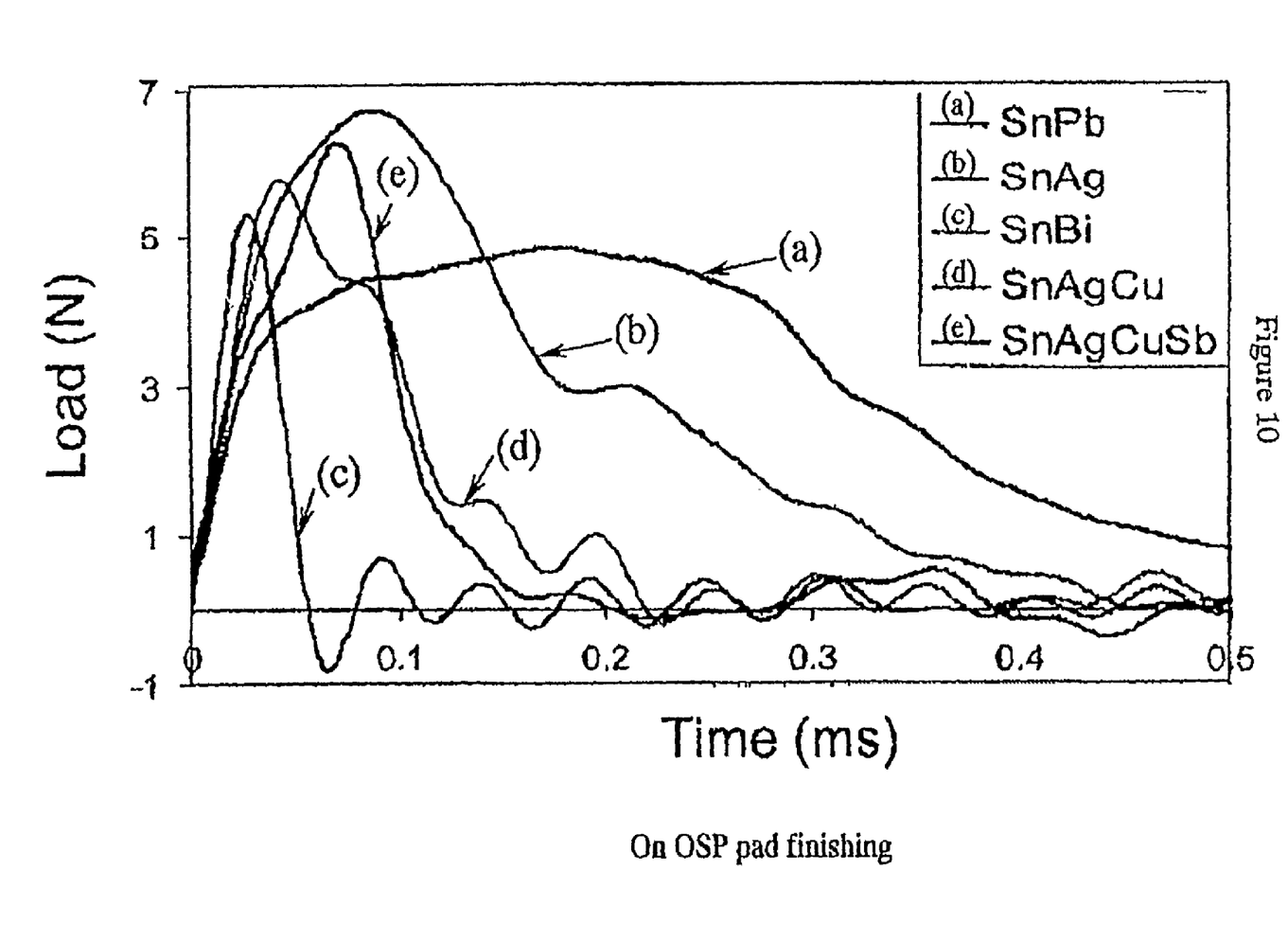
FIG. 10 shows a load against time graph for various tin-based solder alloys when subjected to impact testing using the present apparatus.

FIG. 10 shows a load against time graph for various tin-based solder alloys subjected to impact testing using the embodiment as shown in FIG. 2. The samples consist of solder balls of 400 μm diameter mounted on an organic substrate with an organic surface preservation (OSP) finish. The shear speed applied to the various test samples using the micro-impact testing apparatus was 600 mm/s. The results illustrated in FIG. 8 show that the samples (a) and (b) are more ductile than samples (c)-(e).

The aforementioned description of the various embodiments has been presented for purposes of illustration and description. It is not intended to be exhaustive or to limit the invention to the precise form disclosed, and obviously many modifications and variations are possible in light of the disclosed teaching. It is intended that the scope of the invention be defined by the claims appended hereto.

What is claimed is:

1. A micro-impact testing apparatus for measuring the impact characteristics of a microelectronics specimen exposed to an impact thereon, the apparatus comprising
   a specimen holder for receiving a specimen to be tested, and
   an impact device comprising
      an impact head,
      a support member
      at least one connecting element,
      a first flexural spring,
      wherein the support member is connected to the connecting element in that the first flexural spring is firmly attached with its one end to the support member and with its other end to the connecting element, and
      a second flexural spring being at least substantially identical to said first flexural spring,
      wherein the connecting element is connected to the impact head in that the second flexural spring is firmly attached with its one end to the connecting element and with its other end to the impact head so that the ends of the first and second flexural springs define, in an unloaded state of the flexural springs, a rectangle, whereby the impact head is moveable transversally with respect to the first and second flexural springs along a linear line between a spring-loaded position and an impact position thereof, and
      wherein the specimen holder is aligned with the impact device such that the specimen is arranged in said impact position of the impact head so that the impact head is capable of impacting on the specimen after traveling from its loaded position towards its impact position along said linear line upon release thereof from said loaded position.

2. The micro-impact testing apparatus according to claim 1, further comprising a third and a fourth flexural springs being at least substantially identical to said first flexural spring, wherein the third and the fourth flexural springs are connected to the support member, the connecting element and the impact head, respectively, in the same manner as the first and the second flexural springs.

3. The micro-impact testing apparatus according to claim 1, further comprising a third flexural spring, wherein the third flexural spring is connected to the support member and the connecting element in the same manner as the first flexural spring, so that the ends of the first and the second flexural springs define a rectangle on one side of the second flexural spring, and the ends of the second and the thirds flexural springs define a rectangle on an opposite side of the second flexural spring, and wherein the characteristics of the flexural springs are designed so as to ensure that the impact head is moveable along said linear line.

4. The micro-impact testing apparatus according to claim 1, wherein the flexural springs are arranged on the same side of the impact head in an at least substantially overlapping relationship with respect to each other, when seen in the traveling direction of the impact head.

5. The micro-impact testing apparatus according to claim 1, wherein the flexural springs are connected to one connecting element and arranged on one side of the impact head in an at least substantially overlapping relationship with respect to each other, when seen in the traveling direction of the impact head, and the apparatus further comprises a second set of flexural springs which are at least substantially identical to said flexural springs and are connected to another connecting element on an opposite side of the impact head in an at least substantially overlapping relationship with respect to each other, when seen in the traveling direction of the impact head, so that the arrangement of the flexural springs and the second set of flexural springs is symmetrical to said linear line.

6. The micro-impact testing apparatus according to claim 1, wherein the flexural spring is a monolithic spring, a leaf spring or a notch spring.

7. The micro-impact testing apparatus according to claim 1, wherein the impact head comprises:
   a load element,
   a core rod,
   a load cell, and
   a striker head,
   wherein the load cell, the load element, the striker head are connected to each other by means of the core rod such that the striker head and the core rode extend along said linear line.

8. The micro-impact testing apparatus according to claim 7, wherein the striker head is adapted to apply a shear force on the microelectronics test specimen upon impact.

9. The micro-impact testing apparatus according to claim 7, wherein the support member is provided with a through-hole and the core rod extends through and protrudes outwardly from said through-hole and supported therein by a spring being coaxially mounted on the core rod, wherein one end of the spring is attached to the support member and the other end of the spring is attached to the core rod.

10. The micro-impact testing apparatus according to claim 7, further comprising a linear variable displacement transformer (LVDT) sensor embedded in the support member cylindrically around and coaxially with the through-hole, such that the core rod is, at the most, in sliding contact with the inner surface of the LVDT sensor.

11. The micro-impact testing apparatus according to claim 7, further comprising a speed control block having attachment means to attach, in a releasable manner, to the portion of the core rod that protrudes outwardly from the through-hole of the support member so as to preload the impact head into said loaded position.

12. The impact testing apparatus according to claim 11, wherein the attachment means is a mechanical screw, a clamping device or a magnet.

13. The impact testing apparatus according to claim 11, wherein the speed control block is mounted on the support member via a guide element which provides for an adjustment of the speed control module along a linear line, thereby adjusting the loaded position, and therefore the preload, of the impact head.

14. The micro-impact testing apparatus according to claim 11, wherein the specimen holder comprises a microscope or a charge coupled device (CCD) video camera or a combination thereof and a clamping component adapted to securely hold a test specimen over in the X, Y and Z-axes.

15. The impact testing apparatus according to claim 11, further comprising a specimen temperature variation apparatus adapted to vary the temperature of the environment surrounding the specimen from −40° C. to 100° C.

16. A micro-impact testing apparatus for measuring the impact characteristics of a microelectronics specimen exposed to an impact thereon, the apparatus comprising
   a specimen holder for receiving a specimen to be tested, and
   an impact device comprising
      an impact head,
      a support member,
      at least a first flexural spring being attached with its one end to the support member and with its other end to a first side of the impact head, and
      at least a second flexural spring being at least substantially identical to said first flexural spring and being attached with its one end to the support member and with its other end to a second side of the impact head being opposite to said first side thereof, whereby the impact head is moveable transversally with respect to the flexural springs along a linear line between a spring-loaded position and an impact position, and
   wherein the specimen holder is aligned with the impact device such that the specimen is arranged in said impact position of the impact head so that the impact head is capable of impacting on the specimen after traveling from its loaded position towards its impact position along said linear line upon release thereof from said loaded position.

17. The micro-impact testing apparatus according to claim 16, further comprising an additional even number of substantially identical flexural springs, wherein the even number of flexural springs are connected to the respective elements in the same manner as those of the first and second flexural springs, such that equal numbers of flexural springs are attached on either side of the impact head.

18. The micro-impact testing apparatus according to claim 16, wherein the flexural springs on either side of the impact head are arranged in a side-by-side manner.

19. The micro-impact testing apparatus according to claim 16, wherein the flexural springs on either side of the impact head are arranged in an at least substantially overlapping relationship with each other, when seen in the traveling direction of the impact head.

* * * * *